(12) United States Patent
Anderson (10) Patent No.: US 11,938,061 B2
(45) Date of Patent: Mar. 26, 2024

(54) OPHTHALMOSCOPE MOUNTED FACE SHIELD

(71) Applicant: Nicholas Anderson, Knoxville, TN (US)

(72) Inventor: Nicholas Anderson, Knoxville, TN (US)

(*) Notice: Subject to any disclaimer, the term of this patent is extended or adjusted under 35 U.S.C. 154(b) by 576 days.

(21) Appl. No.: 17/301,676

(22) Filed: Apr. 12, 2021

(65) Prior Publication Data

US 2022/0117788 A1 Apr. 21, 2022

Related U.S. Application Data

(60) Provisional application No. 63/012,866, filed on Apr. 20, 2020, provisional application No. 63/008,074, filed on Apr. 10, 2020.

(51) Int. Cl.
| | |
|---|---|
| *A61F 9/02* | (2006.01) |
| *A41D 13/11* | (2006.01) |
| *A61B 3/12* | (2006.01) |
| *A61B 90/00* | (2016.01) |

(52) U.S. Cl.
CPC .......... *A61F 9/027* (2013.01); *A41D 13/1184* (2013.01); *A61B 3/12* (2013.01); *A61B 90/05* (2016.02)

(58) Field of Classification Search
CPC .......... A61B 3/12; A61B 90/05; A61F 9/027; A41D 13/1184
See application file for complete search history.

(56) References Cited

U.S. PATENT DOCUMENTS

| | | |
|---|---|---|
| 4,955,394 A | 9/1990 | Dean |
| 5,341,513 A | 8/1994 | Klein et al. |
| 6,996,846 B1 | 2/2006 | Karapetyan |
| 2013/0031693 A1 | 2/2013 | Gleason et al. |

*Primary Examiner* — Jack Dinh
(74) *Attorney, Agent, or Firm* — Robinson IP Law, PLLC (57) ABSTRACT

A visor is provided that is adapted to be mounted on a binocular indirect ophthalmoscope. The visor includes: a visor body shaped to conform with at least a portion of the binocular indirect ophthalmoscope; a visor attachment portion located between the visor body and one of a headband, instrument housing, or instrument housing strut of the binocular indirect ophthalmoscope when the visor is mounted on the binocular indirect ophthalmoscope. The visor is mountable on the binocular indirect ophthalmoscope such that the visor body is located in front of a substantial portion of a wearer of the binocular indirect ophthalmoscope. The visor is located on the binocular indirect ophthalmoscope such that the visor does not interfere with operation of the binocular indirect ophthalmoscope during operation of the binocular indirect ophthalmoscope.

1 Claim, 8 Drawing Sheets

*FIG. 9* thalmoscope. The visor is mountable on the binocular indirect ophthalmoscope such that the visor body is located in front of a substantial portion of a wearer of the binocular indirect ophthalmoscope. The visor is located on the binocular indirect ophthalmoscope such that the visor does not interfere with operation of the binocular indirect ophthalmoscope during operation of the binocular indirect ophthalmoscope.

In one embodiment, the visor is movably mounted on one of the headband, instrument housing, and strut of the binocular indirect ophthalmoscope; and the visor is movable between a raised position and a lowered position. In another embodiment, the visor is pivotally mountable on the headband binocular indirect ophthalmoscope. In yet another embodiment, the visor is pivotally mountable on the instrument housing of the binocular indirect ophthalmoscope. In one embodiment, when the visor is in the raised position the binocular indirect ophthalmoscope is mountable on a wall charger.

In another embodiment, the visor attachment portion includes one or more support members, wherein the one or more support members support the visor such that the visor is spaced-apart from the binocular indirect ophthalmoscope.

In yet another embodiment, the visor is mounted on the instrument housing of the binocular indirect ophthalmoscope and the visor attachment portion includes one or more of an adhesive or fasteners. In one embodiment, the visor is mounted on the headband of the binocular indirect ophthalmoscope and the visor attachment portion includes one or more of an adhesive or fasteners.

In another embodiment, the visor is mounted on the binocular indirect ophthalmoscope such that the body is located flush against an illumination window of the instrument housing. In yet another embodiment, the visor is mounted on the binocular indirect ophthalmoscope such that the body is located flush against an eyepiece of the instrument housing.

In one embodiment, the visor further includes a cutout located at the instrument housing such that the visor fits at least partially around the instrument housing of the binocular indirect ophthalmoscope.

In a second aspect, a visor adapted to be mounted on a binocular indirect ophthalmoscope includes: a visor body shaped to conform with at least a portion of the binocular indirect ophthalmoscope; a visor attachment portion located between the visor body and one of a headband, instrument housing, or instrument housing strut of the binocular indirect ophthalmoscope when the visor is mounted on the binocular indirect ophthalmoscope. The visor is movably mountable on the binocular indirect ophthalmoscope such that the visor body is located in front of a substantial portion of a wearer of the binocular indirect ophthalmoscope when the visor is in a lowered position. The visor is located substantially above the binocular indirect ophthalmoscope when the visor is in a raised position. The visor is located on the binocular indirect ophthalmoscope such that the visor does not interfere with operation of the binocular indirect ophthalmoscope during operation of the binocular indirect ophthalmoscope when the visor is in the raised and lowered positions.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Figure 1:
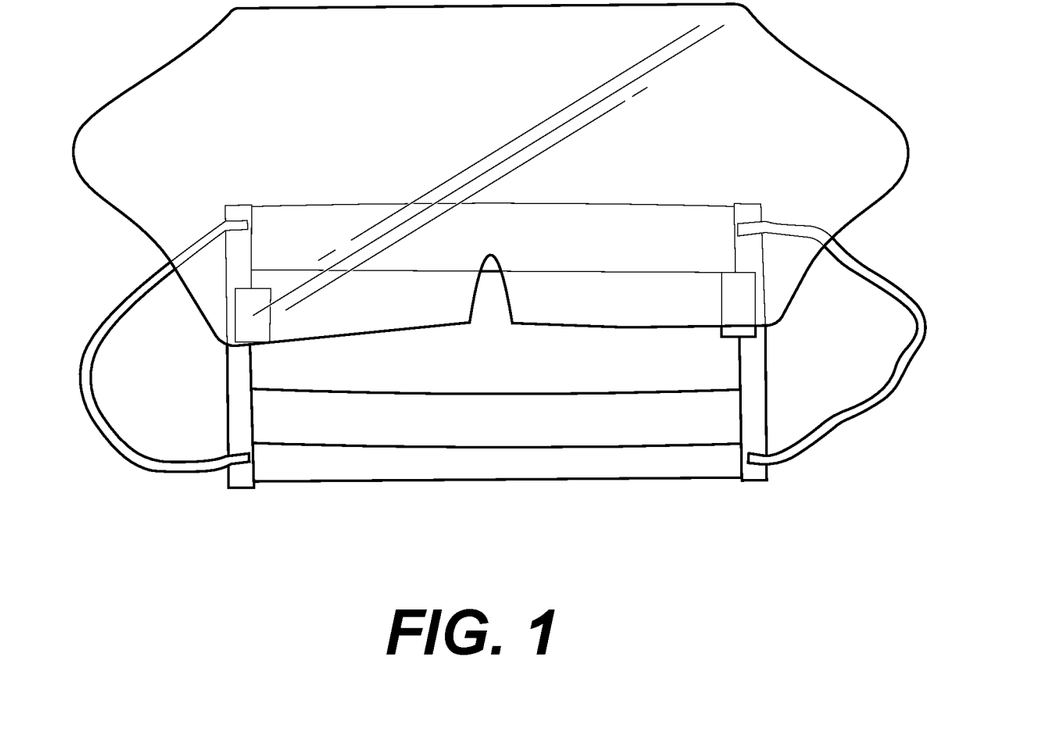
FIG. 1 shows a front view of an existing face mask with a face shield.
Figure 2:
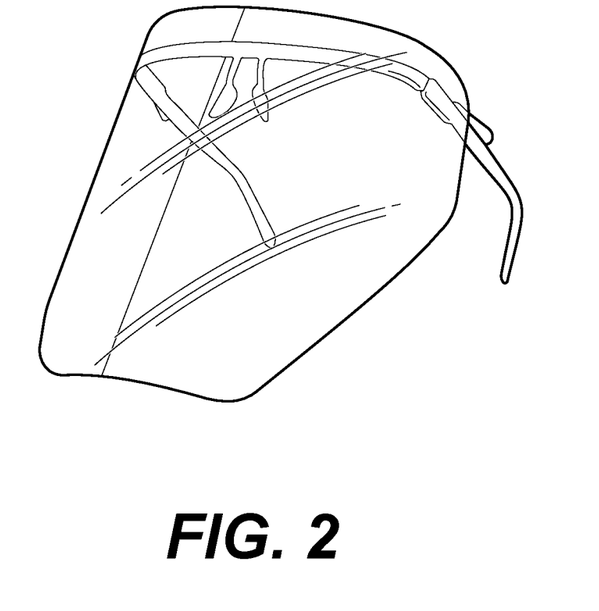
FIG. 2 shows a perspective view of an existing face shield.
Figure 3:
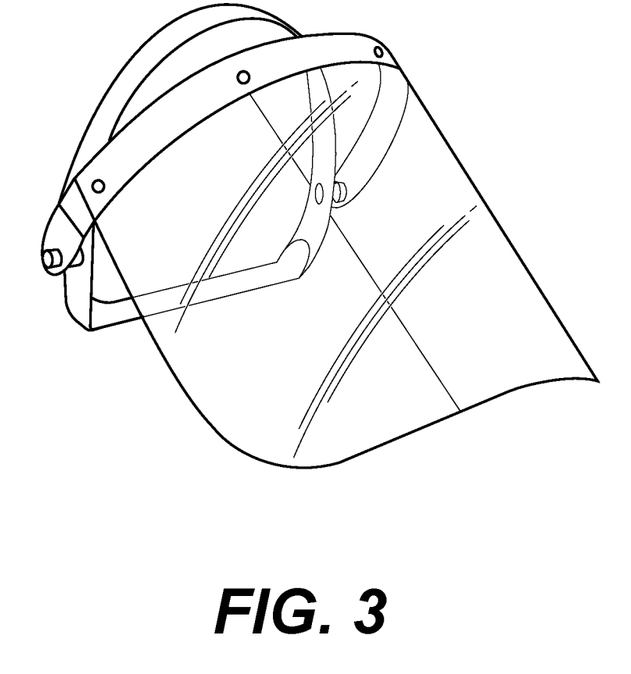
FIG. 3 shows a perspective side view of an existing face shield.
Figure 4:
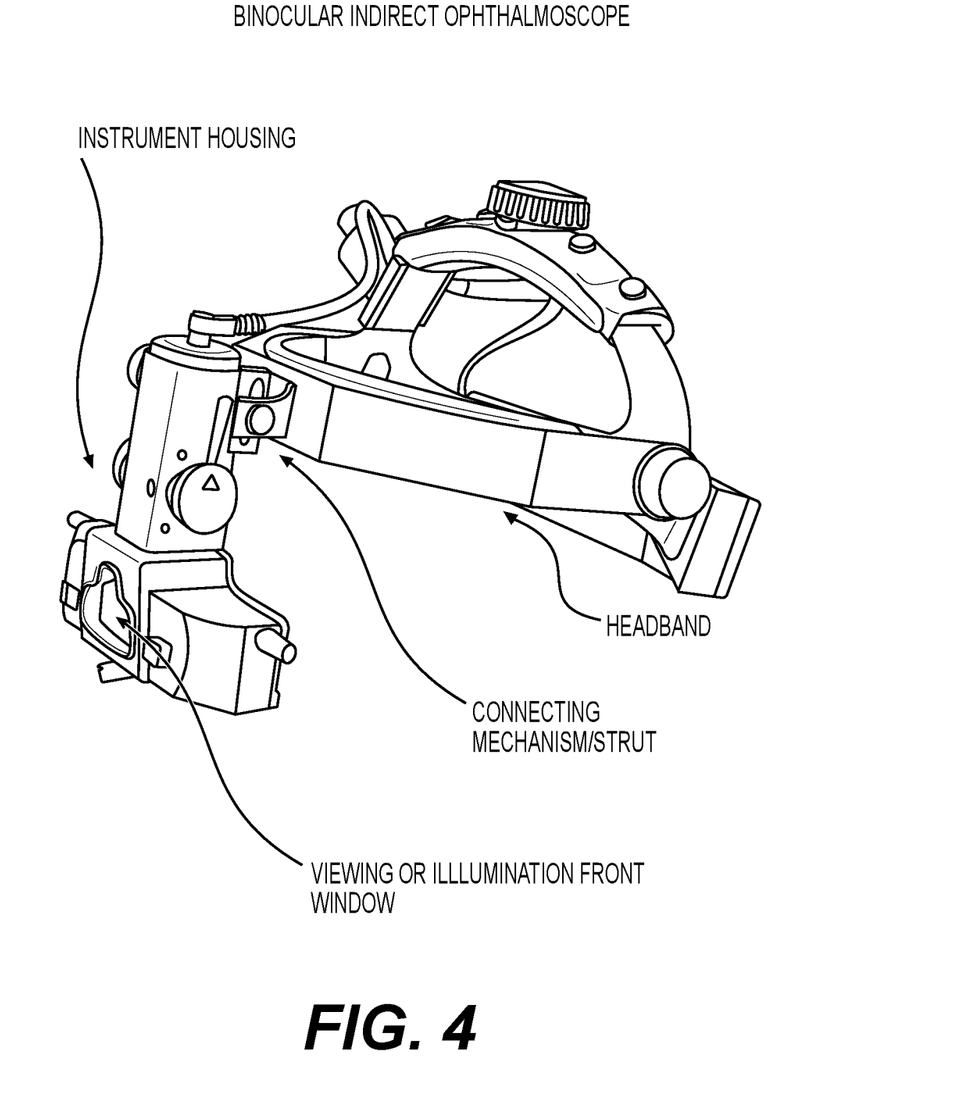
FIG. 4 shows a side view of a binocular indirect ophthalmoscope.
Figure 5:
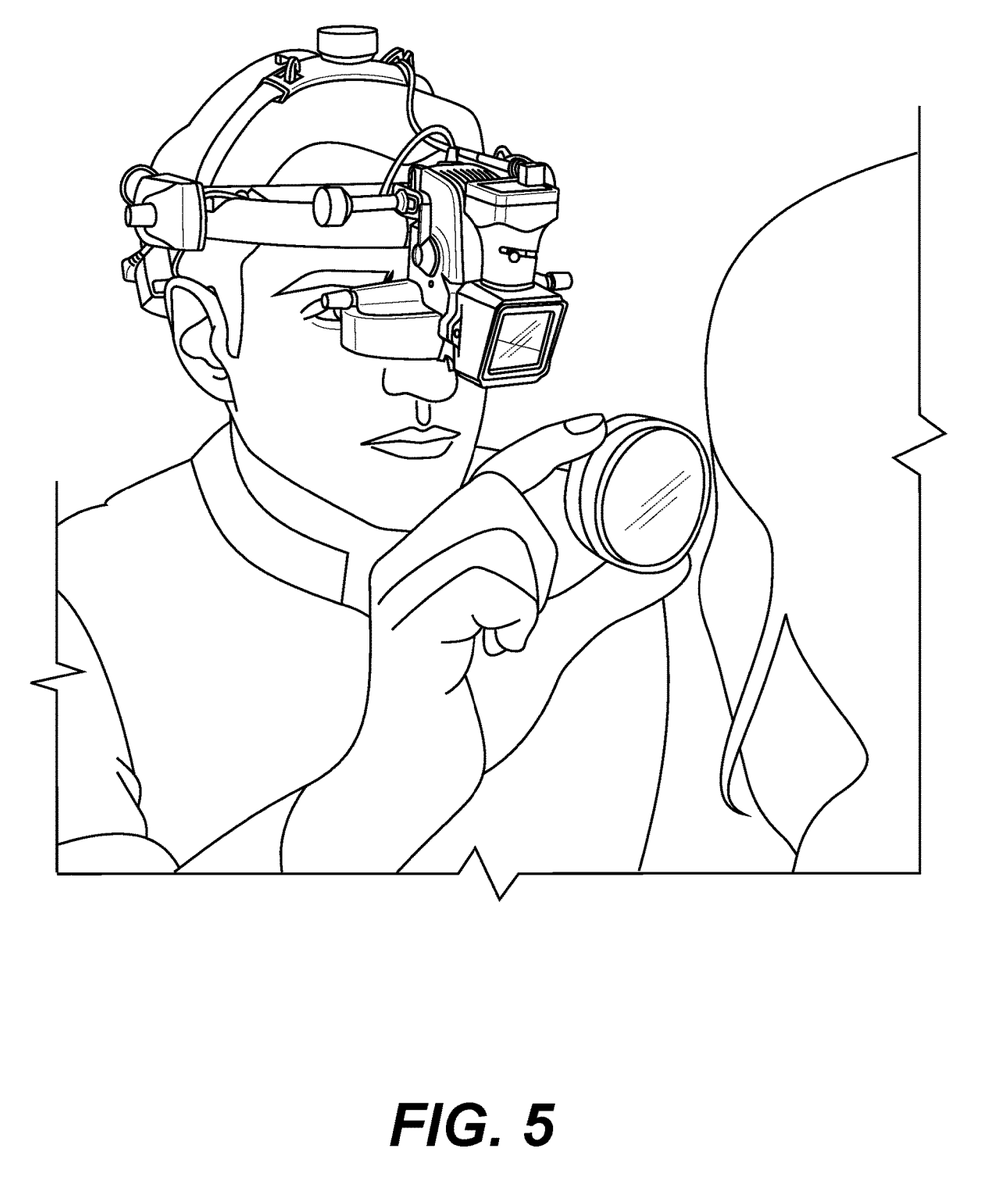
FIG. 5 shows a healthcare provider wearing a binocular indirect ophthalmoscope.
Figure 6:
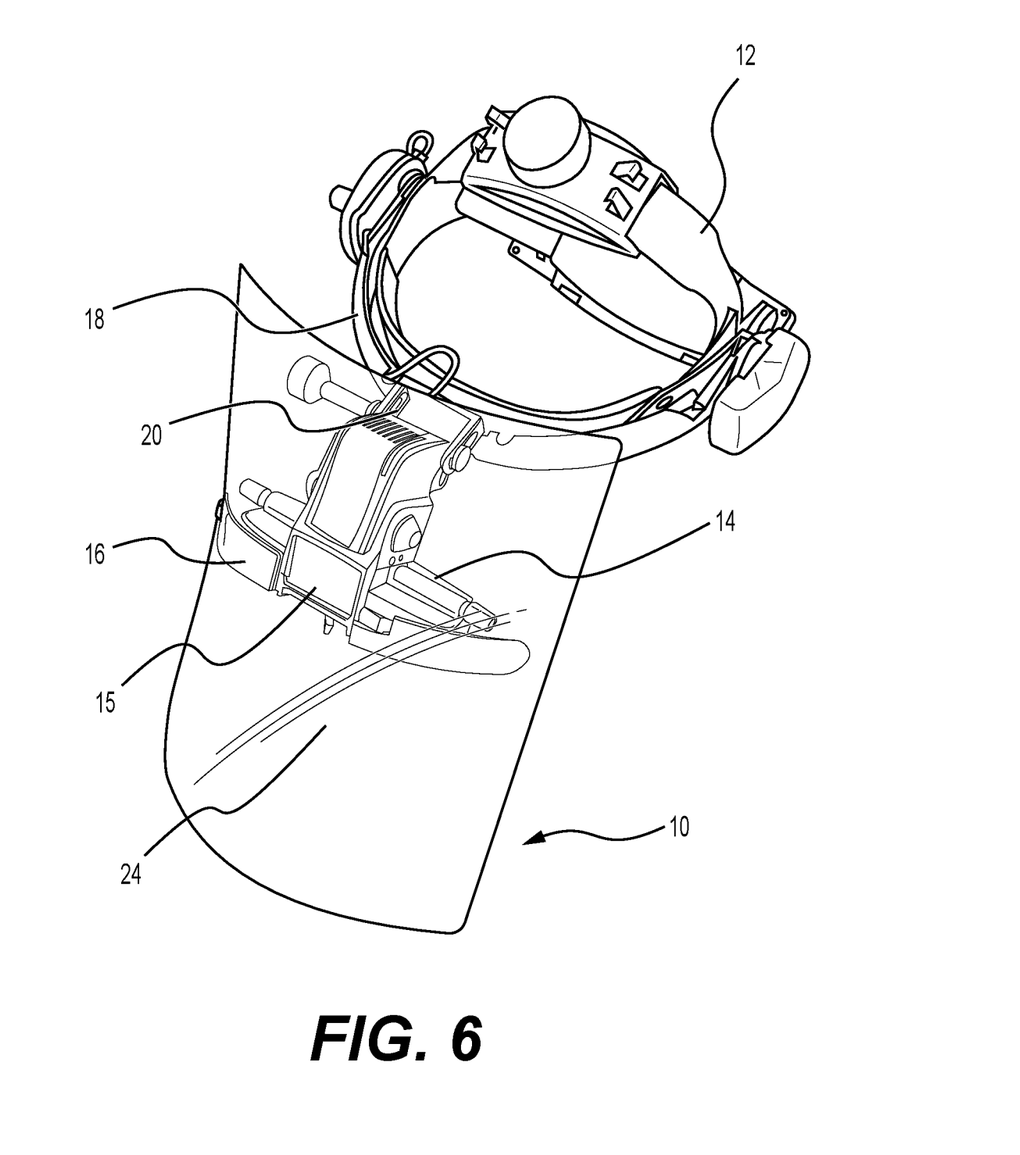
FIG. 6 shows a top perspective view of a visor mounted on a binocular indirect ophthalmoscope according to one embodiment of the present disclosure.

FIG. 6 shows a basic embodiment of a visor 10 mounted on a binocular indirect ophthalmoscope 12. The visor 10 is mounted on the binocular indirect ophthalmoscope 12 such that the visor 10 substantially protects a face of a healthcare provider wearing the binocular indirect ophthalmoscope 12 and is mounted such that the visor 10 does not interfere with use of the binocular indirect ophthalmoscope 12, such as during examination of a patient or during a procedure.

The visor 10 may be bonded or otherwise permanently fixed to an instrument housing 14 of the binocular indirect ophthalmoscope 12. Alternatively, the visor 10 may be located on or form part of an extension of the instrument housing 14. In one embodiment the visor 10 may be located on the instrument housing 14 such that the visor 10 is located in front of the instrument housing 14. Alternatively, the visor 10 may be mounted on the instrument housing 14 such that the visor 10 is located behind the instrument housing 14 towards the face of a healthcare provider wearing the binocular indirect ophthalmoscope 12.

In one example, the visor 10 may be secured to the instrument housing 14 on opposing sides of an illumination window 15 of the instrument housing 14. The visor 10 may be secured, for example, with adhesive strips 16 located between the visor 10 and the instrument housing 14. The adhesive strips 16 or other fasteners used are preferably located on either side of the illumination window 15 such that the illumination window 15 of the binocular indirect ophthalmoscope 12 is not obstructed.

In another embodiment, the visor 10 is removably secured on the binocular indirect ophthalmoscope 12, such as on the instrument housing 14. For example, the visor may be removably secured on the instrument housing 14 using one or more of screws, clips, adhesives, hook and loop fasteners, buttons, snaps, pegs, or sleeves. The visor 10 may be removably secured either in front of the instrument housing 14 or behind the instrument housing 14 of the binocular indirect ophthalmoscope 10.

In one embodiment, the visor 10 is secured on the binocular indirect ophthalmoscope 12 on a headband 18 of the binocular indirect ophthalmoscope 12. The visor 10 may be permanently or removably secured to the headband 16. For example, the visor 10 may be removably secured on the headband 18 using one or more of screws, clips, adhesives, hook and loop fasteners, buttons, snaps, pegs, or sleeves. The visor 10 may be removably secured either in front of the instrument housing 14 or behind the instrument housing 14 of the binocular indirect ophthalmoscope 10.

In yet another embodiment, the visor 10 may be secured on the binocular indirect ophthalmoscope at a strut 20 or other mechanism connecting the instrument housing 14 to the headband 18. The visor 10 may be permanently bonded or mounted to the strut 20 between the instrument housing 14 and the headband 18 of the binocular indirect ophthalmoscope 12. Alternatively, the visor 10 may be removably mounted to the strut 20. For example, the visor 10 may be removably secured on the strut 20 using one or more of screws, clips, adhesives, hook and loop fasteners, buttons, snaps, pegs, or sleeves. The visor 10 may be removably secured either in front of the instrument housing 14 or behind the instrument housing 14 of the binocular indirect ophthalmoscope 10 when the visor 10 is mounted on the strut 20.

The visor 10 may be mounted on the binocular indirect ophthalmoscope 12 using one or more clips or other mechanisms of securing the visor 10 to one of the instrument housing 14, headband 18, or strut 20. For example, a clip or other mechanism for connecting the visor 10 to the binocular indirect ophthalmoscope 12 may be used to secure the visor 10 in front of a face of a wearer of the binocular indirect ophthalmoscope 12. In one embodiment, the visor 10 may be formed in a shape that is adaptable to a plurality of types of the binocular indirect ophthalmoscope 12, such as using one or more clips or other attachment mechanisms.

The visor 10 may be mounted on the binocular indirect ophthalmoscope 12 such that the visor 10 is flush with the illumination window 15 of the binocular indirect ophthalmoscope 12. Alternatively, the visor 10 may be mounted on the binocular indirect ophthalmoscope 12 such that the visor 10 is flush with eyepieces 22 of the binocular indirect ophthalmoscope 12. In another alternative, the visor 10 may be spaced apart from the illumination window 15 or the eyepieces 22 of the binocular indirect ophthalmoscope 12 such that a gap exists between the visor 10 and one of the illumination window 15 and the eyepieces 22 and the visor 10.

The visor 10 may be formed having a visor body 24. The visor body 24 may be substantially flat. Alternatively, the visor body 24 may be curved such that a shape of the visor 10 conforms around a shape of a head of a healthcare provider wearing the visor 10 and the binocular indirect ophthalmoscope 12. The visor body 24 may be placed in front of the illumination window 15 or behind the eyepieces 22. Alternatively, a cutout or hole may be formed through the visor body 24 at the illumination window 15 or the eyepieces 22 such that the visor body 24 is not located within a field of view of the binocular indirect ophthalmoscope 12.

The visor body 24 may be contoured or otherwise shaped to conform to a shape of the binocular indirect ophthalmoscope 12. For example, the visor body 24 may be contoured to conform to a shape of one or more of the instrument housing 14, the headband 18, or the strut 20 of the binocular indirect ophthalmoscope 12. The visor body 24 may be secured on the binocular indirect ophthalmoscope 12 at one or more switches or dials 26 of the binocular indirect ophthalmoscope 12. In one embodiment, the visor 10 is secured on the binocular indirect ophthalmoscope 12 such that the visor 10 angles away from a face of a wearer of the binocular indirect ophthalmoscope 12 to create additional space for the healthcare provider to breathe.

Figure 7:
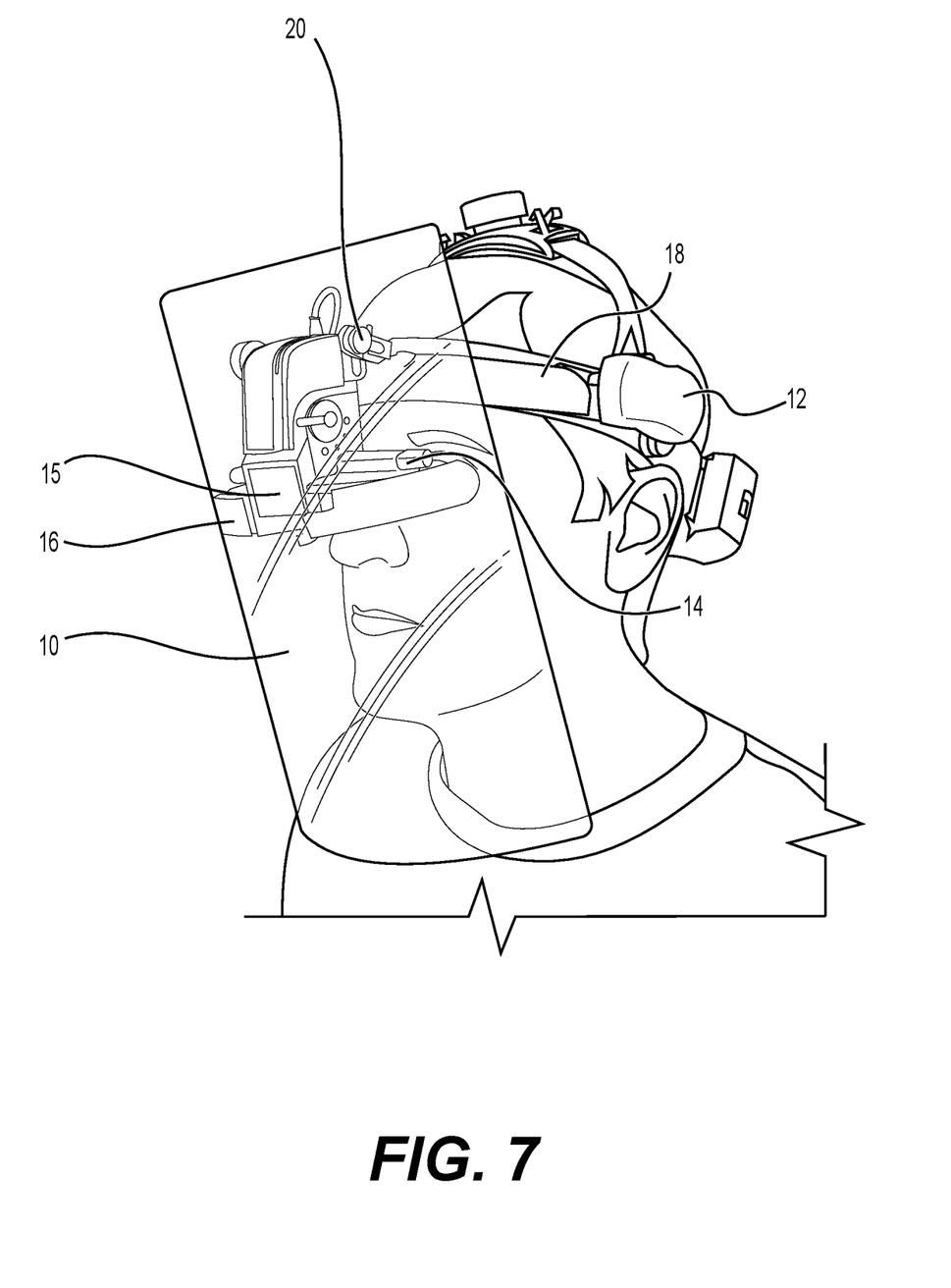
FIG. 7 shows a side view of a visor mounted on a binocular indirect ophthalmoscope according to one embodiment of the present disclosure.
Figure 8:
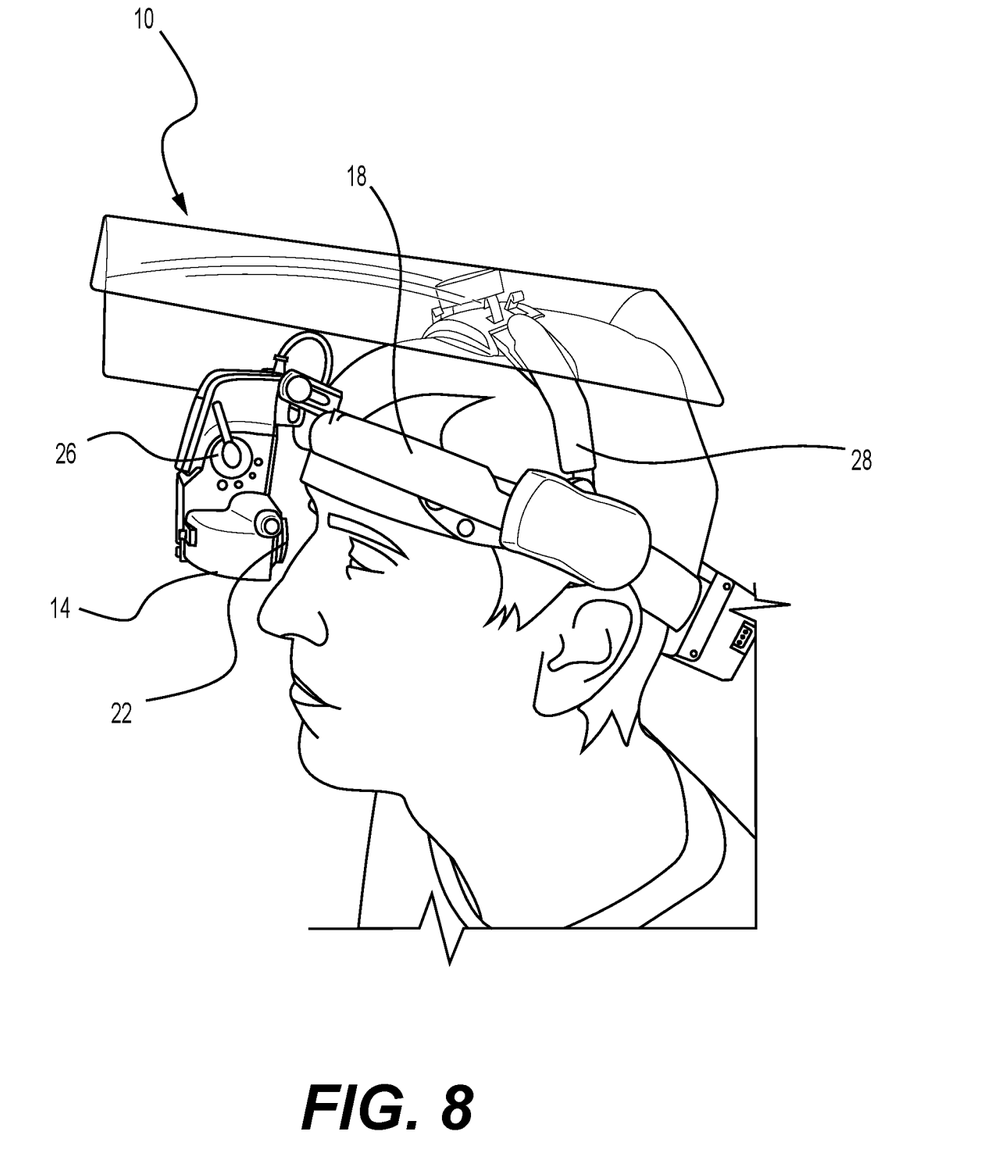
FIG. 8 shows a side view of a visor mounted on a binocular indirect ophthalmoscope with the visor in a raised position according to one embodiment of the present disclosure.
Figure 9:
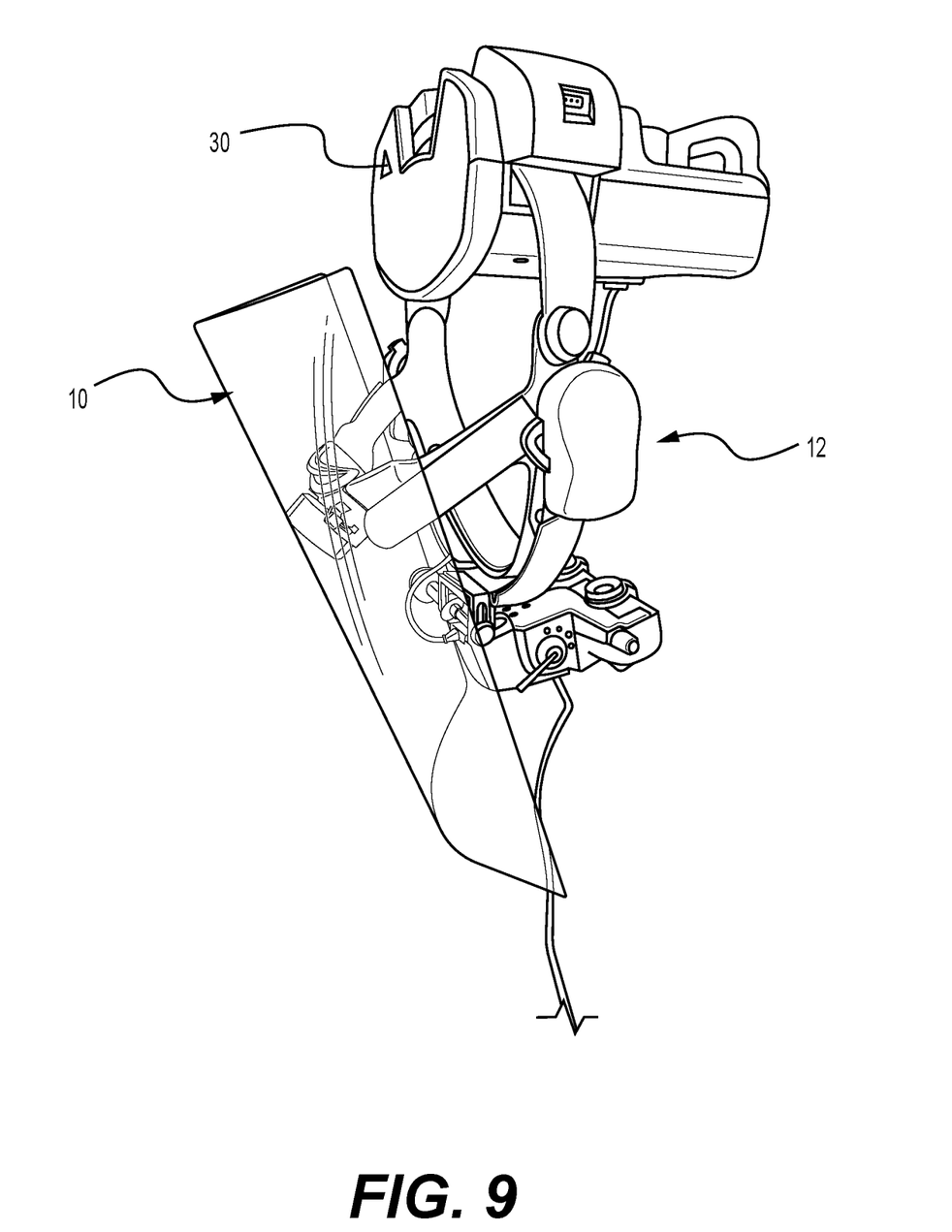
FIG. 9 shows a side view of a visor mounted on a binocular indirect ophthalmoscope during charging of the binocular indirect ophthalmoscope according to one embodiment of the present disclosure.

The visor 10 may be fixed in position relative to the binocular indirect ophthalmoscope 12. Alternatively, the visor 10 may be secured on the binocular indirect ophthalmoscope 12 such that the visor 10 may pivot between a raised position (FIG. 8) and a lowered position (FIG. 7). In the raised position, the visor 10 is located such that the visor body 24 is not over a face of the healthcare provider. In the lowered position, the visor body 24 is located proximate to the face of the healthcare provider to substantially protect the face of the healthcare provider. The visor 10 may be secured on the binocular indirect ophthalmoscope 12 at a pivot, such as with one or more axles, ball and socket joints, hinges, or other suitable components for allowing the visor 10 to pivot with respect to the binocular indirect ophthalmoscope 12. In one embodiment, the visor 10 is pivotally mounted on the binocular indirect ophthalmoscope 12 with one or more support members 28 such that the visor 10 is spaced-apart from the binocular indirect ophthalmoscope 12. The one or more support members 28 may be pivotally mounted on the binocular indirect ophthalmoscope 12 to allow the visor 10 to pivot between the raised and lowered positions. When the visor 10 is in the raised position, the visor 10 is oriented relative to the binocular indirect ophthalmoscope 12 such that the binocular indirect ophthalmoscope 12 may be placed on a charger 30 or hanging from a wall, as shown in FIG. 9.

In operation, a healthcare provider may don the binocular indirect ophthalmoscope 12 having the visor 10 secured thereon on the healthcare provider's head, using the headband 18 to support the instrument housing 14 and instruments contained therein in front of the wearer's eyes. The healthcare provider may adjust a position of the instrument housing 14 to a suitable location in front of the wearer's face, as shown in FIG. 7. A light source is illuminated and shines light on an eye of a patient using a handheld condensing lens. The healthcare provider then views the patient's eye using the binocular indirect ophthalmoscope while performing an examination, procedure, or surgery. The visor 10 protects a face and head of the wearer of the binocular indirect ophthalmoscope while providing a clear view through the visor 10. The visor 10 may be rotated or otherwise moved to the raised position (FIG. 8) while the visor 10 is not in use or not needed, or while the binocular indirect ophthalmoscope 12 is resting on the charger 30 (FIG. 9).

By securing the visor 10 to the binocular indirect ophthalmoscope 12 according to embodiments described herein, various problems are solved. First, the visor 10 may be properly positioned relative to the strut 20, the instrument housing 14, the headband 18, or other components of the binocular indirect ophthalmoscope 12 without interfering with those components, thereby allowing proper positioning of both the visor 10 and components of the binocular indirect ophthalmoscope 12. Second, by securing the visor 10 on the binocular indirect ophthalmoscope 12, a separate headband for the visor 10 or other means of supporting the visor 10 on the healthcare provider's head is eliminated such that no interference exists between a support of the visor 10 and the binocular indirect ophthalmoscope 12. Third, the visor 10 may be placed in an appropriate position over the face of the healthcare provider without causing any deflection of the visor 10 from the instrument housing 14 or other components of the binocular indirect ophthalmoscope 12. Fourth, embodiments of the visor 10 described herein will not cause the visor 10 to be pressed uncomfortably against a nose, mouth, or face of the wearer, and will not prevent the use of a facemask being worn by the healthcare provider. Fifth, any glare or light reflections from the visor may be reduced or eliminated by providing a controlled distance and angle between the visor and binocular indirect ophthalmoscope 12 illumination or illumination window 15. Sixth, by locating the visor 10 on the binocular indirect ophthalmoscope 12 as disclosed herein, adequate space for air flow between the wearer's face and the visor 10 is provided to reduce or eliminate fogging due to condensation from breathing, sweating, or ambient humidity. Seventh, by allowing the visor 10 to move between raised and lowered positions relative to the binocular indirect ophthalmoscope 12, the healthcare provider may move the visor 10 out of a field of view of the healthcare provider when the visor 10 is not needed. Eighth, allowing the visor 10 to pivot between raised and lowered positions further allows the binocular indirect ophthalmoscope 12 to be used with a wall-mounted charger or holder without the visor 10 contacting the wall or otherwise obstructing the binocular indirect ophthalmoscope 12 from being located on the wall-mounted charger or holder.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A visor adapted to be mounted on a binocular indirect ophthalmoscope, the visor comprising:
    a visor body;
    a visor attachment portion, the visor attachment portion located between the visor body and one of a headband, instrument housing, or instrument housing strut of the binocular indirect ophthalmoscope when the visor is mounted on the binocular indirect ophthalmoscope;
    wherein the visor is movably mountable on the binocular indirect ophthalmoscope such that the visor body is located in front of a substantial portion of a wearer of the binocular indirect ophthalmoscope when the visor is in a lowered position;
    wherein the visor is located substantially above the binocular indirect ophthalmoscope when the visor is in a raised position;
    wherein when the visor is mounted on the binocular indirect ophthalmoscope the body is located flush against an illumination window of the instrument housing; and
    wherein the visor is located on the binocular indirect ophthalmoscope such that the visor does not interfere with operation of the binocular indirect ophthalmoscope during operation of the binocular indirect ophthalmoscope when the visor is in the raised and lowered positions.

* * * * *